United States Patent [19]

Riehm et al.

[11] 4,239,922

[45] Dec. 16, 1980

[54] XYLOSE AND XYLITOL SEPARATELY PURIFIED IN SAME ION EXCHANGER

[75] Inventors: Theodor Riehm, Heidelberg; Theodor Auel, Ilvesheim; Wilhelm Spatz, Ober-Kainsbach, all of Fed. Rep. of Germany

[73] Assignee: Benckiser-Knapsack GmbH, Ladenburg, Fed. Rep. of Germany

[21] Appl. No.: 48,074

[22] Filed: Jun. 13, 1979

[30] Foreign Application Priority Data

Jun. 22, 1978 [DE] Fed. Rep. of Germany ....... 2827477

[51] Int. Cl.$^3$ ............................................ C07C 31/18
[52] U.S. Cl. .................... 568/863; 560/872
[58] Field of Search ............................ 568/863, 872

[56] References Cited

U.S. PATENT DOCUMENTS

| | | | |
|---|---|---|---|
| 2,917,390 | 12/1959 | Apel et al. | 568/863 |
| 2,989,569 | 6/1961 | Apel | 568/863 |
| 3,558,725 | 1/1971 | Kohno et al. | 568/863 |
| 3,579,380 | 5/1971 | Friese | 568/863 |
| 3,627,636 | 12/1971 | Jaffe et al. | 568/863 |
| 3,784,408 | 1/1974 | Jaffe et al. | 568/863 |
| 3,980,719 | 9/1976 | Buckl et al. | 568/863 |
| 4,066,711 | 1/1978 | Melaja et al. | 568/872 |

Primary Examiner—Joseph E. Evans
Attorney, Agent, or Firm—Schwartz, Jeffery, Schwaab, Mack, Blumenthal & Koch

[57] ABSTRACT

A process for producing polyalcohols such as xylite from deciduous wood wherein the wood is hydrolyzed with dilute mineral acid to produce a sugar solution which is deionized and decolorized in an ion exchanger and hydrogenated to produce a polyalcohol solution which is also decolorized and deionized by ion exchange and from which pure polyalcohol is thereafter separated by crystallization, further comprising dispensing with neutralization of the acid in the sugar solution after hydrolysis, deionizing and decolorizing both the sugar solution and the polyalcohol solution in the same ion exchanger, eluting acetic acid taken up by the ion exchanger from the polyalcohol solution and displacing polyalcohol solution from the exchanger with the acid containing sugar solution, washing the ion exchanger with water only after ion exchange of the sugar solution, removing the bulk of the acetic acid from the sugar solution by evaporating the sugar solution to a higher concentration than the concentration customarily utilized for hydrogenation, and rediluting the sugar solution prior to hydrogenation with the exchanger wash water.

7 Claims, 4 Drawing Figures

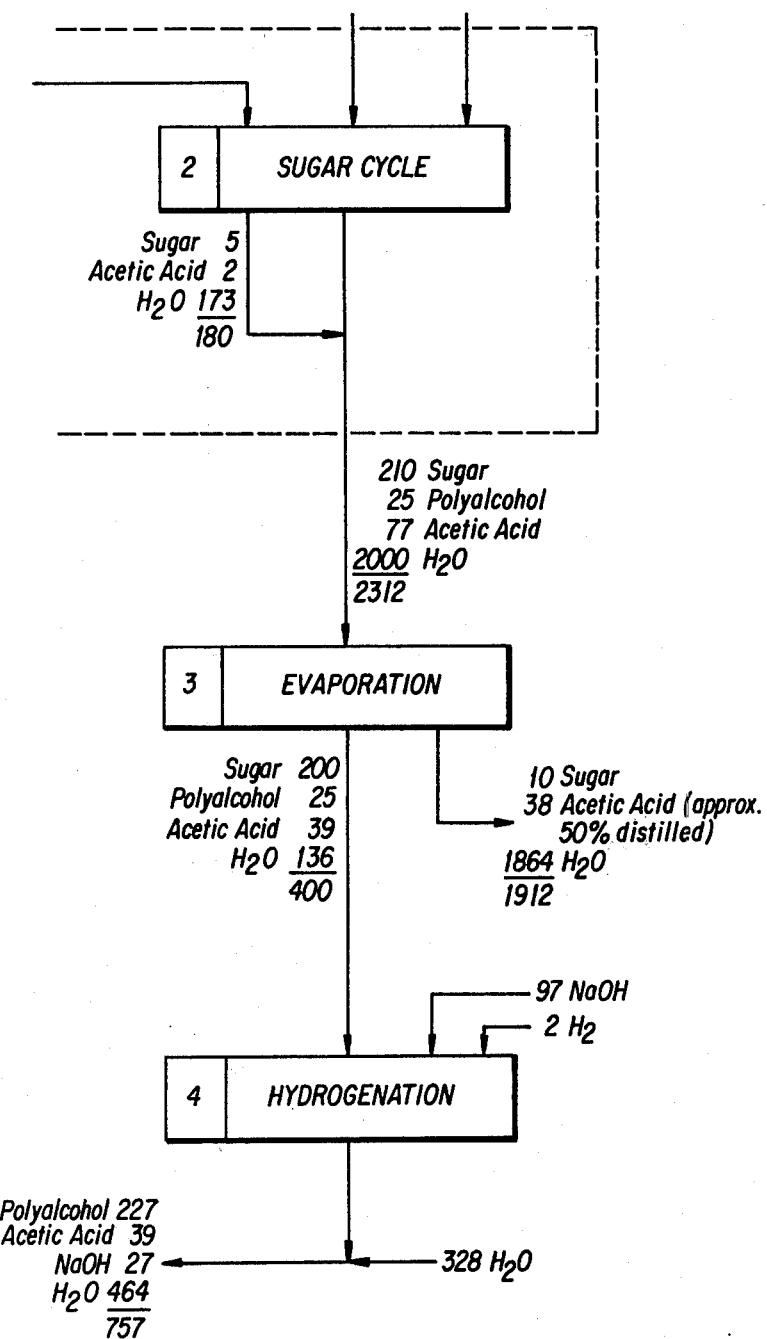
FIG. 2a COMPARISON WITHOUT FEATURES OF CLAIM 5

XYLOSE AND XYLITOL SEPARATELY PURIFIED IN SAME ION EXCHANGER

BACKGROUND OF THE INVENTION

This invention relates to a process for the production of polyalcohols, particularly xylite (or xylitol as it is sometimes termed) from the wood of deciduous trees or annual plants by decomposition with dilute mineral acid at elevated temperatures, decolorization and deionization with ion exchangers, and hydrogenation.

Numerous processes are known to produce in particular xylose and xylite from the wood of deciduous trees or from annual plants. Most of the processes, especially those practiced on an industrial scale, comprise the following series of process steps (Cf. *Die Hefen,* Volume II, Pages 82 to 113 (1962); Festkrift TILLAGNAD GUNNAR SUNDBLAD, Oct. 10, 1958, Ivar Haeggstroms Boktryckeri AB, Pages 75ff; West German Auslegeschriften Nos. 16 43 940; 25 30 386 and 23 50 668; and French Pat. No. 14 77 305):

1. Acid hydrolysis of the plant material with dilute mineral acids, especially sulfuric acid or hydrochloric acid, at temperatures of 100° to approximately 135° C.
2. Neutralization with lime and gypsum filtration (only in the case of sulfuric acid hydrolysis).
3. Removal of salts, organic acids, especially acetic acid, and coloring matter by means of ion exchangers, carbon and decolorizing resins.
4. Evaporation and crystallization of xylose.
5. Hydrogenation of xylose with Raney nickel at 30 to 50 atmospheres after previously adjusting the pH. Usually the xylose mother-liquor is also hydrogenated to polyalcohols.
6. Repeated deionization and evaporation of the xylite solution or the polyalcohol solution as the case may be.
7. Crystallization and drying of the xylite.

Variants of the above-described process steps additionally consist of an alkaline, acid or alcoholic prewashing prior to the actual hydrolysis, as may be seen for example, in the German Offenlegunsschriften Nos. 23 58 407 and 25 22 761. The process of the present invention does not require these process steps.

In any of these cases, the production of xylite on an industrial scale is only possible in a series of numerous process steps with concomitant high production costs. To date, this has prevented widespread use of this sugar substitute, even though its pleasant taste, its sweetening power comparable to sucrose, its acceptability for diabetics and especially its proven anticaries properties and unobjectionable nature from a health standpoint, make xylite a highly interesting substance from an economic viewpoint.

The aforementioned numerous process steps are represented in FIG. 1 which is a material flow sheet for a typical, true to practice example of a prior art process.

Known process steps or parts of the installation are listed in boxes in sequence from top to bottom. The connecting lines represent mass flows, whereby the numbers written alongside the lines signify quantities of material in kg. in reference to or calculated for 1000 kg. of dry wood. Hydrolysis is effected by means of a sugar containing approximately 1.2% sulfuric acid solution at 120° to 130° C. The recycling of wash water results in hydrolysates containing approximately 7.8% sugar and also containing the amounts of acetic acid, sulfuric acid and cations (calculated as CaO) listed in FIG. 1.

According to investigations performed, after neutralization with lime and filtration of the gypsum obtained in the process, 22 kg. sulfuric acid and 22 kg. CaO remain in solution as shown in FIG. 1 because of the increased solubility of gypsum in the presence of sugar, whereby the CaO content has more than doubled with respect to the original hydrolysis solution. As a result of the washing of the gypsum and the subsequent addition of the wash water, the sugar solution is diluted by approximately 1/10. Furthermore, there is a sugar loss of about 1%.

In FIG. 1, the ion exchange according to the data cited in German Pat. No. 11 83 870 has been taken into consideration, whereby 65 kg. acetic acid remain in solution in order to avoid the expensive anion exchange of the acetic acid. In the sugar evaporation step, the solution is evaporated to approximately 80% sugar, whereby approximately 80% of the acetic acid is distilled off and there is, together with the ion exchange process, another sugar loss of approximately 5%.

For the sake of simplicity, the subsequent xylose crystallization is represented in FIG. 1 as a single step. In reality, this stage includes a series of successive crystallization steps, together with the steps of evaporating and recycling the liquors which are necessary to obtain the recited xylose yields. During crystallization, there is another loss of sugar, amounting to approximately 2.5%. An approximately 50% aqueous solution is prepared from the crystallized xylose, and a base is added to adjust the pH and buffer the solution. Hydrogenation follows in the usual manner.

After hydrogenation, the solution is diluted to approximately 30% to render ion exchange possible. This is followed by evaporation and crystallization, which are also represented in simplified fashion as single steps in the flow sheet of FIG. 1, but which include several crystallizations and liquor evaporations, which are necessary, as in the crystallization of xylose, to achieve high xylite yields. In the ion exchange process and the evaporation during the xylite stage, there are again losses of approximately 5%.

The economical conduct of the process requires utilization of the xylose liquor, which is usually converted to high value end products by hydrogenation to polyalcohols. This is also shown in FIG. 1. The acetic acid (13 kg.) that has not been distilled off is concentrated in the xylose liquor and is removed from the polyalcohol by ion exchange. The final xylite liquor is added to the polyalcohol, as seen in FIG. 1, note 5.

A summary of the factors from the above-described sequence of conventional process steps which primarily determine the costs of xylite and other polyalcohols, shows these factors to be:

1. The amount of cations to be bound, i.e., as CaO and NaOH, as well as the amount of anions to be bound as $H_2SO_4$ and acetic acid. These amounts determine the size of the entire ion of the exchange installation and the attendant investment, operating and regeneration costs. They represent a highly significant cost factor of the entire xylite production process.
2. The sum of the sugar losses in the different process stages.
3. The total amount of water to be evaporated in all of the process stages.

This amount determines in the investment cost of all evaporating installations and their energy consumption as further important cost factors of xylite production.

The following Table 1 summarizes these factors in numerical fashion with respect to 1000 kg. of dry wood.

TABLE I

| | Cation exchange kg of CaO equivalents (CaO + NaOH) | Anion exchange kg of $H_2SO_4$ equivalents | Sugar losses kg | Evaporation of water kg $H_2O$ |
|---|---|---|---|---|
| Gypsum filtration | | | 2 | |
| Ion exchange and evaporation of the sugar solution | 22 | 25 | 10 | 2992 |
| Xylose crystallization | | | 5 | |
| Xylite ion exchange and evaporation | 1 | 1 | 5 | 317 |
| Polyalcohol ion exchange and evaporation | 6 | 12 | 4 | 184 |
| Totals | 29 | 35 | 26 | 3493 |

SUMMARY OF THE INVENTION

The present invention is based on the following features which together constitute the process of the invention.

Surprisingly, it has proven possible with the process of the present invention to simplify or even eliminate various process steps by carrying out the decolorization and ion exchange of the sugar solution and of the polyalcohol solution in the same ion exchanger.

DESCRIPTION OF THE PREFERRED EMBODIMENT

Figure 1A:
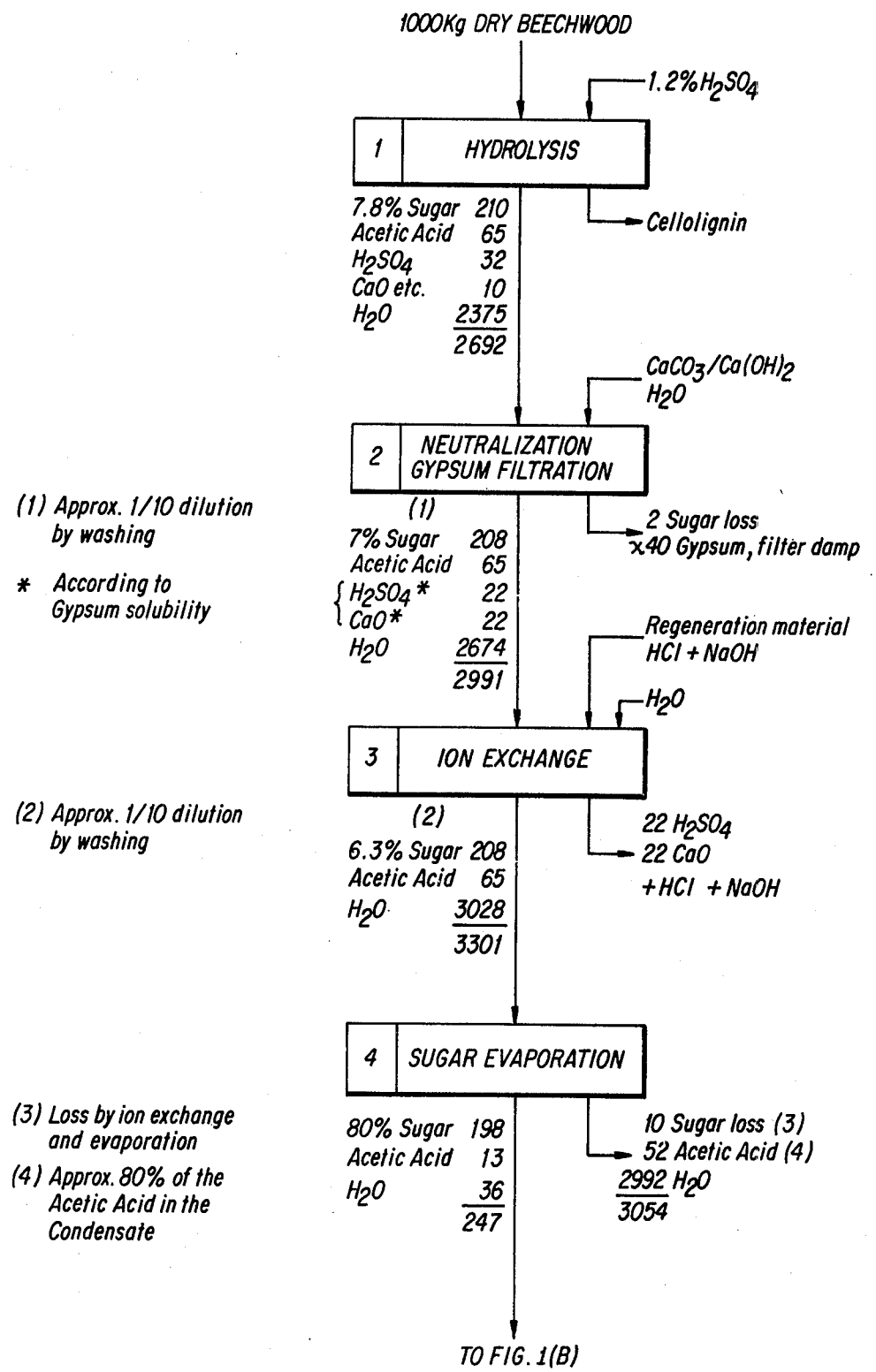
Figure 1B:
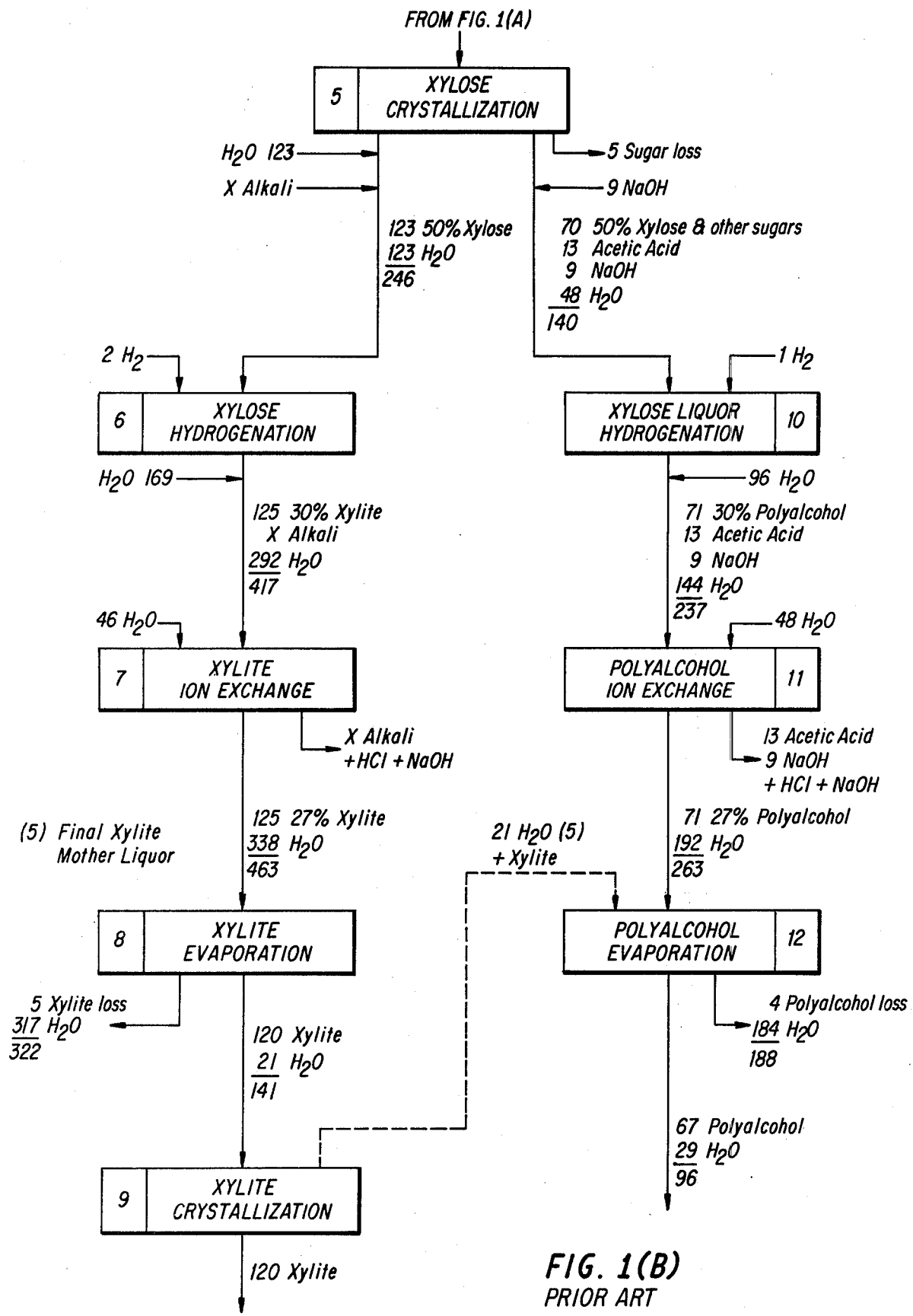
Figure 2:
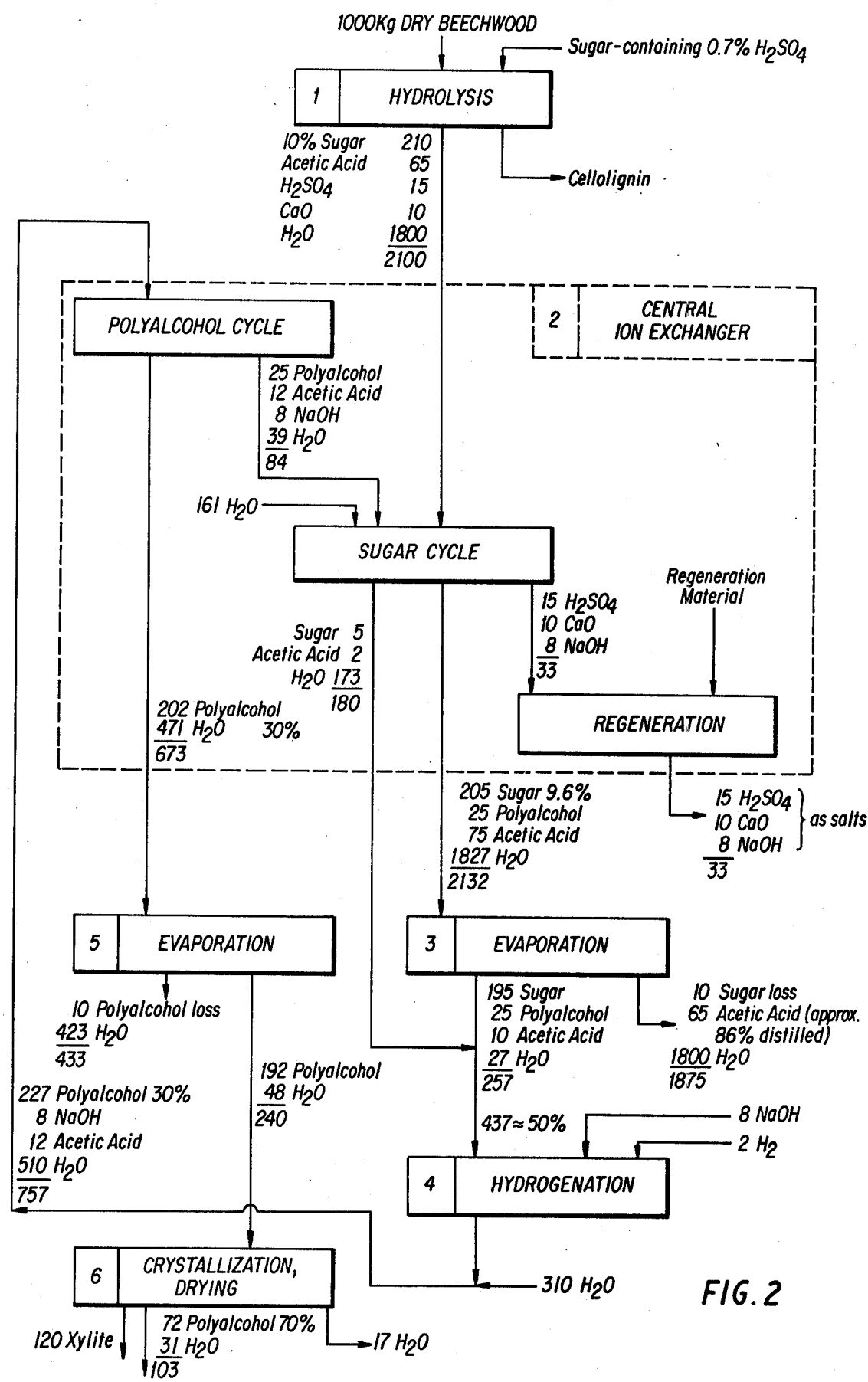

The individual steps of the process of the present invention are represented in the material flow sheet of FIG. 2 which illustrates a process that is readily carried out. In accordance with FIG. 1, the quantities shown in FIG. 2 are with reference to an input of 1000 kg of dry wood so that a direct comparison with FIG. 1 is possible.

In the practical embodiment of the process of the present invention, the sulfuric acid used for the hydrolysis or decomposition step is applied in such a concentration that neutralization by calcium carbonate or calcium hydroxide is unnecessary. To attain this object, sulfuric acid is used in a concentration of 0.4 to 0.8%, preferably 0.7% at temperatures of 140° to 160° C., preferably 150° C., and heated for approximately 2 hours. This saves not only the process costs of gypsum precipitation and filtration but also avoids the higher cation exchange process costs usually caused by the added neutralizing agent. By connecting at least two or three hydrolysis columns in sequence, sugar concentrations of approximately 10% may be obtained without substantial losses of sugar, as can be seen from FIG. 2.

The unusual dual function of the exchanger installation has very significant consequence with respect to the plant size and production costs of the xylite process. This results in a substantial saving in investment costs, regeneration costs and evaporation costs.

According to the present invention, the newly regenerated exchanger installation is initially fed a weakly colored polyalcohol solution with a low anion and cation content. In the installation, which at this point is greatly overdimensioned, the polyalcohols are completely freed of cations and anions as well as organic acids and coloring agents. The result is a highly purified polyalcohol solution, so that especially high crystallization yields may be obtained as a result of the purity of the solution. It should be particularly emphasized that the same xylite yield of approximately 120 kg is obtained even without the expensive xylose crystallization stage. It is further seen in FIG. 2 that the 12 kg of residual acetic acid from the hydrogenated solution are bound by the exchanger and pass into the sugar cycle.

Following the polyalcohol cycle, the heretofore lightly occupied ion exchange and decoloration installation, is operated in the sugar cycle up to full capacity with the sugar solution obtained after the decomposition process, with its very much higher cation and anion concentrations. The cation content amounts to approximately 10 kg as CaO and the anion content to approximately 15 kg as $H_2SO_4$. Thus, in the sugar cycle the capacity of the exchanger installation is fully utilized, whereby slight breakthroughs of ions are not harmful, because there is no subsequent xylose crystallization stage. Such breakthroughs have been neglected in FIG. 2. Ion traces that may have broken through are removed during the final purification in the polyalcohol cycle, prior to the xylite crystallization.

In the sugar cycle, the acetic acid absorbed during the polyalcohol cycle (12 kg) and the bound proportion of acetic acid from the exchanger installation, will be completely eluted from the exchanger installation by the stronger sulfuric acid (15 kg). This makes it possible to remove all of the organic acid (65 kg) in the subsequent evaporation stage by distillation from the sugar solution instead of in the expensive ion exchange process. A small amount of the organic acid (10 kg according to FIG. 2) remains in the sugar solution but is recirculated and is finally removed by distillation. The separation of acetic acid by distillation is disproportionally less expensive than by anion exchange, the more so since distillation is required in any case to obtain higher sugar concentrations. The acetic acid may then be recovered from the condensate by rectification of liquid-liquid extraction.

Following the sugar cycle and prior to regeneration, the exchanger installation is washed in the convention manner with 161 kg water, so that no sugar will be lost with the regenerating waters. In contrast to the usual mode of operation, the exchanger, despite its dual function, is washed with water only in the sugar cycle. During the transition from the polyalcohol cycle to the sugar cycle, the polyalcohol with its greater specific gravity, is forced out of the resin bed from top to bottom by the lighter sugar solution. In view of the very sharp transition from polyalcohol to sugar in the lower outflow of the exchanger, the switch from "polyalcohol evaporation" (left production stream in FIG. 2) to sugar may be effected very rapidly, so that traces of polyalcohol may appear in the flow of sugar, but not sugar in the polyalcohol stream. The polyalcohol content in the sugar solution is immaterial, because it does not increase the load on the exchanger. By eliminating the need for two washes, the total amount of water to be evaporated is reduced. Only during the hydrogenation is there an additional load created on the reactor volume, negligible within the context of the total process, by the small amount of polyalcohol carried in circulation, which may be captured by means of an only slightly increased overall concentration.

In order to obtain a high acetic acid distillation rate, evaporation is carried substantially further than convenient for hydrogenation. A technical limit is established by the viscosity of the sugar solution. In accordance with FIG. 2, a distillation rate of approximately 86% of the acetic acid is achieved with an 85% sugar+polyalcohol solution.

In order to dilute the 85% solution to 50% for hydrogenation, the wash solution from the sugar cycle of the exchanger, which has to be evaporated in any case, is utilized in place of fresh water. According to FIG. 2, 180 kg of a solution directly from the exchanger containing about 5 kg sugar are used to dilute the 85% sugar solution. In this manner, no more water has to be evaporated than if the total solution were evaporated to 50%.

The less favorable case is illustrated in FIG. 2a for the sake of comparison. Therein, 39 kg acetic acid would be recirculated in place of 10 kg, and to neutralize the acetic acid 27 kg NaOH would be required in place of 8 kg, which later would have to be eliminated by means of cation exchange.

In Table 2, hereinbelow, the factors affecting the cost of the process according to the invention are compiled for comparison with the conventional process according to Table 1.

TABLE 2

| | Cation exchange kg of CaO equivalents (CaO + NaOH) | Anion exchange kg of $H_2SO_4$ equivalents | Sugar losses kg | Evaporation of water kg of $H_2O$ |
|---|---|---|---|---|
| Central ion exchange | 15 | 15 | | |
| Sugar evaporation | | | 10 | 1800 |
| Polyalcohol evaporation | | | 10 | 423 |
| Polyalcohol post-evaporation | | | | 17 |
| Totals | 15 | 15 | 20 | 2240 |
| Compare Table 1 | 29 | 35 | 26 | 3493 |

The conventional process requires twelve installation components, the process of the present invention only six. The comparison shows that in the process according to the invention the number of installation components is reduced by one-half. Additionally, the volume of the exchanger is reduced by 48 and 57%, corresponding to the CaO and the $H_2SO_4$. Furthermore, in keeping with the above-described evaporation of water, a single evaporator is sufficient, the dimensions and energy consumption of which are reduced by 36%. Also, the loss of sugar in processing is reduced by approximately 23% because of the lower number of process steps involved.

The foregoing description has been set forth solely as an example of the invention. Since modifications of the disclosed embodiment may occur to persons skilled in the art, the scope of the invention is to be limited solely by the scope of the appended claims.

We claim:

1. A process for producing xylitol comprising the steps of: decomposing the wood of deciduous trees or annual plants with dilute mineral acid at elevated temperatures to produce a solution containing principally xylose sugar with minor proportions of acetic acid and mineral salts; subjecting the sugar solution to ion exchange treatment and decolorization in an exchanger; hydrogenating the sugar solution to produce a polyalcohol solution containing principally xylitol; subjecting the polyalcohol solution to an ion exchange treatment; and thereafter recovering xylitol from the solution; said exchange treatment of the sugar solution and exchange treatment of the polyalcohol solution being effected in separate sugar and polyalcohol cycles in the same exchanger.

2. A process according to claim 1, wherein the exchanger is regenerated; the regenerated exchanger is initially charged with a polyalcohol solution containing acetic acid produced during decomposition of the wood, and the acetic acid contained in the polyalcohol solution is bound in the exchanger, said exchanger thereafter being fed a mineral acid containing sugar solution, and the acetic acid is eluted from the exchanger by means of the mineral acid in said sugar solution.

3. A process according to claim 1 or 2 wherein following the ion exchange of the polyalcohol solution, the higher specific gravity polyalcohol solution remaining in the exchanger after passage of the polyalcohol solution therethrough is displaced from top to bottom by the lower specific gravity sugar solution and that the exchanger is washed and regenerated with water only after the sugar cycle.

4. A process according to claim 1, wherein the ion exchanger is washed with water following the ion exchange treatment of the sugar solution; the sugar solution is evaporated to a concentration substantially in excess of the concentration customarily used for hydrogenation in order to separate the acetic acid generated by hydrolysis, and the sugar solution is thereafter diluted with the wash water from the sugar cycle of the exchanger to a concentration suitable for hydrogenation.

5. A process according to claim 1, wherein the entire sugar solution obtained after decomposition of the wood and ion exchange treatment of the resulting sugar solution is concentrated by evaporation and hydrogenated, and xylitol is obtained from the total polyalcohol solution by crystallization following further ion exchange purification and evaporation.

6. A process according to claim 1, wherein decomposition is effected by treatment with a 0.4 to 0.8% sulfuric acid solution at 140° to 160° C., for a period of approximately 2 hours, without subsequent neutralization with calcium salts.

7. A process according to claim 6 wherein decomposition is effected with a 0.7% sulfuric acid solution at a temperature of about 150° C.

* * * * *